ALSTROEMERIA PLANT (CANARIA)

Filed April 9, 1971 2 Sheets-Sheet 1

INVENTOR.
MAURITS C. VAN STAAVEREN

BY Rummler & Snow
ATTYS.

ALSTROEMERIA PLANT (CANARIA)

Filed April 9, 1971 2 Sheets-Sheet 2

United States Patent Office

Plant Pat. 3,283

Patented Jan. 2, 1973

3,283

ALSTROEMERIA PLANT (CANARIA)

Maurits C. van Staaveren, 30 Hornweg, Aalsmeer, Netherlands

Filed Apr. 9, 1971, Ser. No. 132,918

Int. Cl. A01h *5/00*

U.S. Cl. Plt.—68 1 Claim

ABSTRACT OF THE DISCLOSURE

A new variety of hybrid alstroemeria plant characterized by the novel overall yellow coloring of its flowers, the abundance of its annual crop of flower stalks, the serial blooming of the buds on each branch of the flower stalk, and the very long-lasting quality of the blooming plant as a cut flower.

BACKGROUND OF THE INVENTION

This new variety of alstroemeria plant originated as a sport of the alstroemeria hybrid "Orchid" and was discovered by me in 1968 in a greenhouse at Aalsmeer, Holland, the parent plant having been roentgen radiated at the I.T.A.L. Institute at Wageningen, Holland. The very pleasing and unusual color of this sport led to its being selected for propagation and trial, and asexual reproduction of the new plant through several generations at Aalsmeer, Holland, has demonstrated that the new variety has retained all of the advantageous qualities of its parent, as well as the novel and distinctive coloring of the discovery sport. Propagation of the new variety is carried on by dividing the rootstock since the plant (male and female) is sterile and commercial production of the new variety is now being done at Aalsmeer, Holland, for entry into the 1971 market.

DESCRIPTION OF THE DRAWINGS

This new variety of alstroemeria plant is illustrated in the accompanying drawings, which show the color characteristics of the blossoms as nearly true as it is reasonably possible to obtain by conventional photographic processes and in which.

DESCRIPTION OF THE NEW PLANT

The following is a detailed description of my new variety of alstroemeria plant with the color designations according to the R.H.S. Colour Chart of the Royal Horticultural Society of London, England.

*The plant*

Origin: Sport.

Parentage: Alstroemeria hybrid "Orchid" (unpatented).

Form: Herb. A tall, slender flower stalk with flower-bearing branches in umbel arrangement at its top.

Height: 1.5 to 2.0 meters at maturity.

Growth: Vigorous and upright.

Rootstock: Tuberous. Tubers grow about 15 cm. per year and each bears 40 to 50 buds during the year, from which the flower stalks grow in various stages of development during the course of the year.

Figure 1:
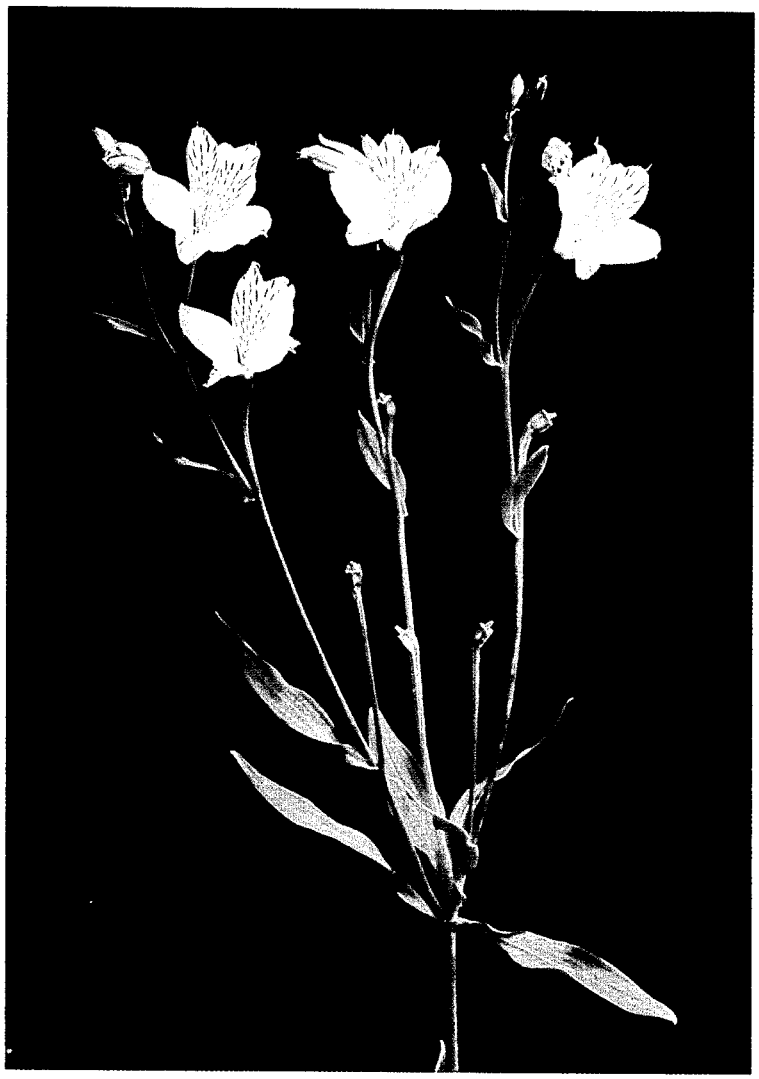
FIG. 1 is a view showing the umbel or branching portion of a typical flower stalk of the new plant in about the middle stage of its blooming period.

Branching: 3 to 7 (average) flower-bearing branches grow at the top of each flower stalk. The branches are in umbel arrangement and each is 30 to 50 cm. long and bears 5 to 7 (average 6) buds spaced apart 3 to 9 cm. along the branch stem. (See FIG. 1.)

Foliage—Leaves:

*Quantity.*—About 20 to 30 leaves are spaced along the flower stalk stem. At branching umbel a circle of leaves is formed, there being one leaf for each branch.

*Shape of leaf.*—Long and narrow, generally linear with acuminate tip, curled at about 1.5 cm. from the stem to turn the morphological underside upward.

*Size of leaf.*—10 to 12 cm. long x 2.0 to 2.25 cm. wide.

*Texture.*—Soft. Appearance: Shiny.

*Color.*—Upper side—Yellow-Green 146A. Under side—Greyed-Green 191A.

*The bud*

Form: Young bud, 12 days before opening—pear shaped, #5 in FIG. 2. Mature bud, just before opening—long and pointed, #6 in FIG. 2.

Size: Just before opening—2.5 cm. long.

Color: Mainly Yellow-Green 145B with slight shade of Red-Purple 60D at tip and base ends. Veins between base and tip are also Red-Purple 60D.

*The flower*

Blooming habit: Recurrent. Twice a year from March to end of May and from mid-August to end of October, in Holland. The flowering in fall season is less abundant than in the spring.

Figure 3:
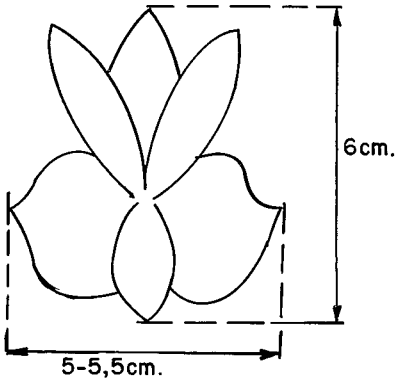
FIG. 3 is a sketch showing the face-view arrangement of the flower petals.
Figure 4:
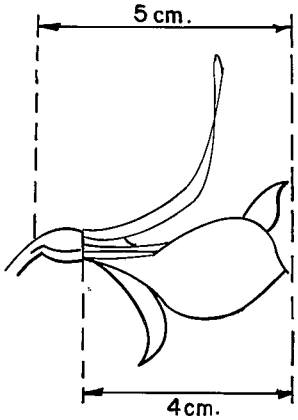
FIG. 4 is a sketch showing the side-view arrangement of the flower petals.

Size: Medium—5 cm. long x 5 to 6 cm. diameter or spread of petals in face view. See FIGS. 3 and 4.

Borne: Singly on long peduncle. 5 to 7 buds on each branch bloom successively, one after the other, about 3 days apart.

Shape: Generally funnel-like.

Petalage: 6 in number, arranged in two concentric circles of 3 petals.

Figure 2:
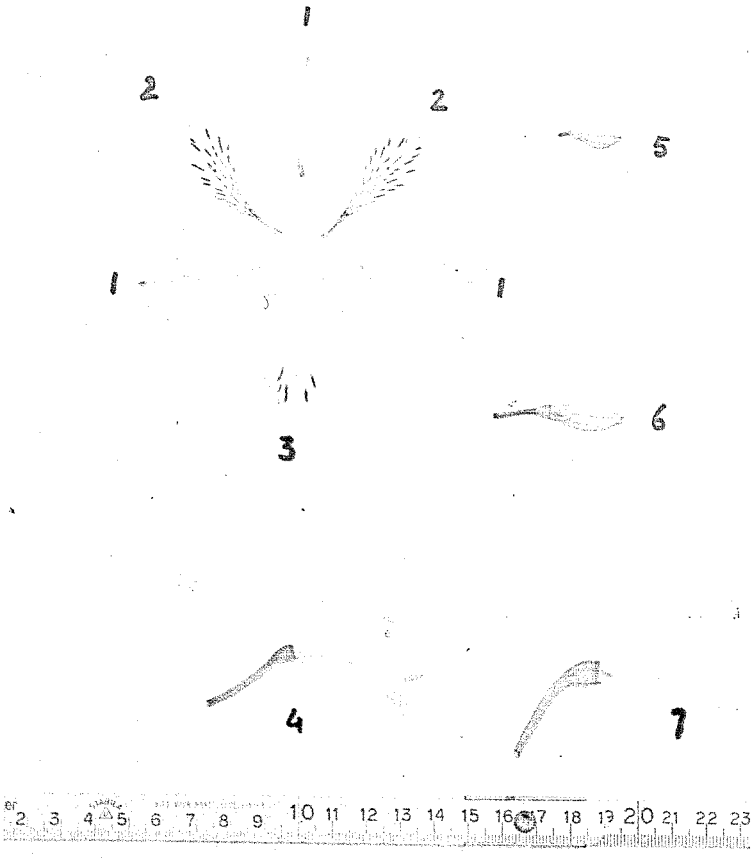
FIG. 2 shows the petals and reproductive organs of a typical flower, young and mature buds, and a specimen of fruit.

*Form.*—Outer petals—#1 in FIG. 2—generally obovate with entire margin and each has a nectary-like base end. Inner petals—upper pair—#2 in FIG. 2—spatulate with entire margin, long nectary at base, and mucronate tip. Lower petal—#3 in FIG. 2—generally obovate with mucronate tip.

*Color.*—Outer petals—Yellow 8A crossed with veins of Green 141C. Inner petals—Yellow-Orange 14A with lengthwise striped of Greyed-Orange 166A.

*Texture.*—Soft.

*Appearance.*—Velvety.

Effect of weather: Color, texture and appearance are not affected by wet or hot weather.

Lasting quality: On plant—10 days for each flower. As cut flower—7 days for each flower and up to 20 days for the umbel of flowering branches.

*Reproductive organs*

Stamens (#4 in FIG. 2):

*Anthers.*—6 in number, 0.7 cm. long, arranged one opposite each petal, and colored Yellow-Green 153B.

*Filaments.*—3.5 to 4 cm. long and Yellow-Orange 14B in color.

Pollen: Color—Yellow-Orange 14B.

Pistil: One only. Length 3.0 cm.

Stigmas: 3 in number and Yellow-Orange 14B in color.

*The fruit*

Generally round in shape—#7 in FIG. 2 and capsular in form with three internal compartments each containing two rows of ovaries attached to the central standing placenta. No seeds are produced and plant is infertile.

This new variety of alstroemeria plant retains all of the desirable characteristics of its commercially-successful parent "Orchid," except the color of its blooms. The new variety has flower petals of an overall yellow color whereas the parent plant has blossoms with white and yellow petals. The pleasing bright yellow of the flowers of the new variety makes it a valuable addition to the known varieties of alstroemeria hybrids.

I claim:

1. The new and distinct variety of alstroemeria plant substantially as herein shown and described, characterized by the distinctive bright yellow overall coloring of its flowers, its abundant, twice-yearly production of blooms, and the long-lasting quality of the blooming plant as a cut flower.

No references cited.

ROBERT E. BAGWILL, Primary Examiner